United States Patent [19]

Aufranc, deceased et al.

[11] 4,095,601
[45] Jun. 20, 1978

[54] ELECTROTHERAPEUTIC APPARATUS

[76] Inventors: Charles Walter Aufranc, deceased, late of Rheineck, Switzerland; by Ida Aufranc, heir, Buhofstrasse 49, 9424 Rheineck, Switzerland

[21] Appl. No.: 692,459

[22] Filed: Jun. 3, 1976

[30] Foreign Application Priority Data

Jun. 9, 1975 Switzerland .................... 7381/75

[51] Int. Cl.$^2$ .............................................. A61N 1/04
[52] U.S. Cl. .................................. 128/405; 128/24.4; 128/422
[58] Field of Search ............... 128/404, 405, 406, 410, 128/411, 419 R, 420–423, 24.3–24.5, 57

[56] References Cited

U.S. PATENT DOCUMENTS

| 745,128 | 11/1903 | Williams | 128/404 |
|---|---|---|---|
| 1,703,811 | 2/1929 | Blum | 128/24.3 |
| 3,163,166 | 12/1964 | Brant et al. | 128/405 |
| 3,180,338 | 4/1965 | Moss et al. | 128/422 |
| 3,255,753 | 6/1966 | Wing | 128/421 |
| 3,373,747 | 3/1968 | Tapper | 128/422 |
| 3,464,416 | 9/1969 | Williams | 128/410 |
| 3,902,502 | 9/1975 | Liss et al. | 128/422 |

FOREIGN PATENT DOCUMENTS

| 1,016,332 | 11/1952 | France | 128/24.3 |
|---|---|---|---|
| 547,642 | 4/1974 | Switzerland | 128/405 |
| 962,695 | 7/1964 | United Kingdom | 128/422 |

*Primary Examiner*—Kyle L. Howell
*Assistant Examiner*—Lee S. Cohen
*Attorney, Agent, or Firm*—Werner W. Kleeman

[57] ABSTRACT

An electrotherapeutic apparatus for external application comprising circuitry for generating direct-current voltage pulses having an amplitude between 4 and 22 volts and a frequency amounting to at least approximately 8.5 Hz.

4 Claims, 5 Drawing Figures

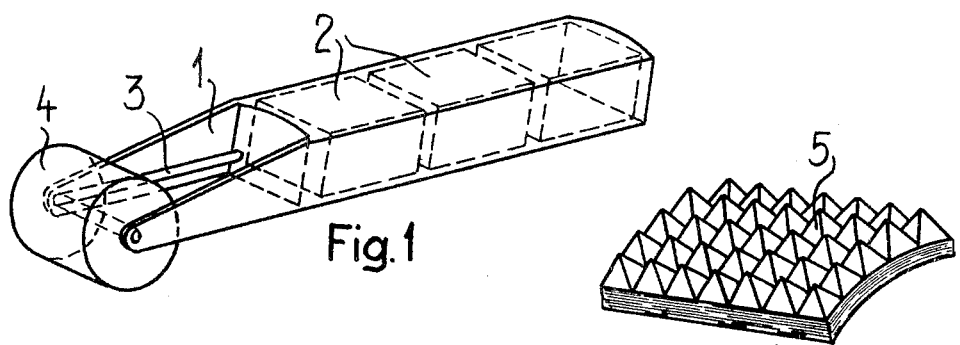
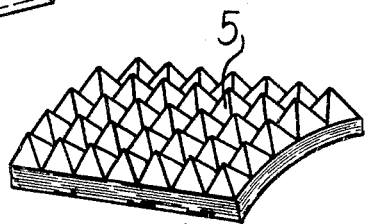
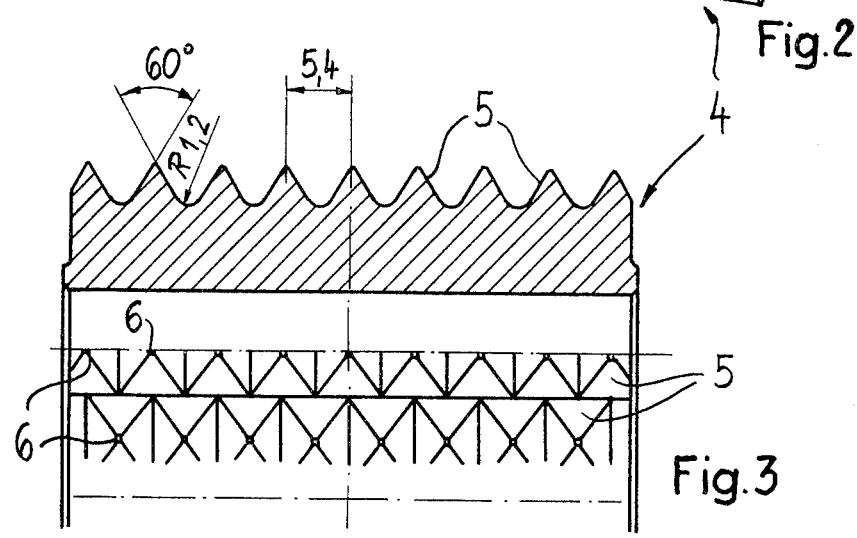
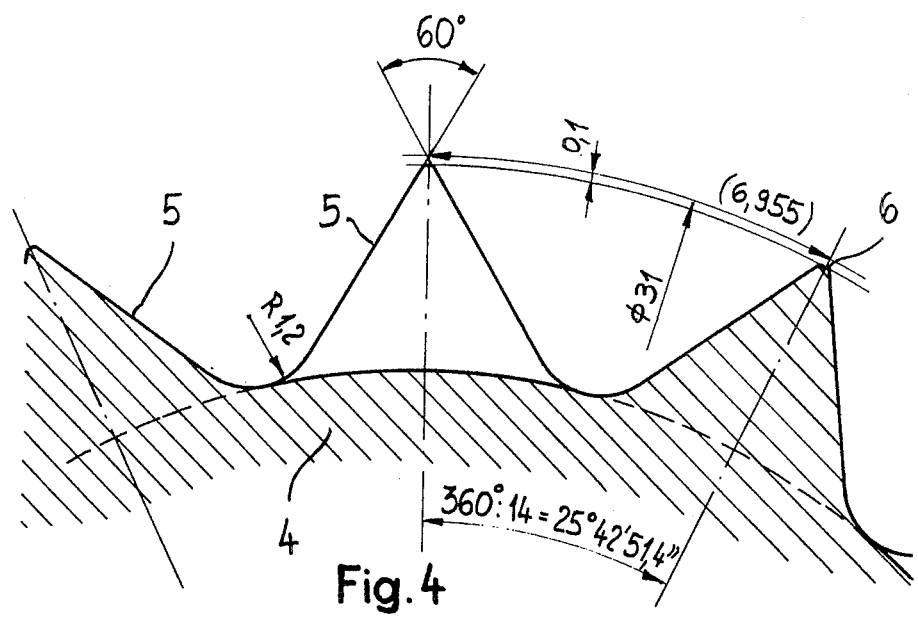

ELECTROTHERAPEUTIC APPARATUS

BACKGROUND OF THE INVENTION

The present invention relates to a new and improved construction of an electrotherapeutic apparatus.

In Swiss Pat. No. 547,642 there is disclosed an electrotherapeutic apparatus for external applications incorporating means for generating direct-current voltage pulses, the amplitude of which is less than 120 volts and the duration of which is less than 0.20 seconds. Now it has been surprisingly found, however, that the effectiveness of the apparatus can be quite considerably increased and the field of application markedly enlarged if the amplitude and duration of the direct-current voltage pulses lie within a narrow, exactly defined range.

SUMMARY OF THE INVENTION

Hence, it is a primary object of the present invention to provide an improved construction of electrotherapeutic apparatus of the previously mentioned type constituting an improvement upon the prior art constructions, specifically that disclosed in the aforementioned Swiss patent.

Accordingly, the present invention is concerned with an apparatus of the previously mentioned type which is manifested by the features that there is provided a circuit for producing direct-current voltage pulses, the amplitude of which is between 6 and 16 volts, preferably 12 volts, and the frequency also in these instances at least amounts to approximately 8.5 Hz.

Preferably there are provided means for generating a square wave voltage course wherein the pulse duration essentially is equal to the time span between two successive pulses. However, this relationship is preferably 60 to 40. In order to transmit such pulses there is most suitable an electrode in the form of a roller, the surface of which consists of pyramid-shaped parts having a substantially quadratic or square flattened portion at the region of their tips, the side length of which advantageously amounts to 0.5 mm. The pyramid-shaped parts can be arranged in rows oriented according to surface lines and these rows can be offset relative to one another, whereby the spacing of the geometric tips of neighboring parts located in successive rows preferably amounts to 6.955mm.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 is a perspective view of an apparatus of the invention provided with a substantially roller-shaped electrode;

FIG. 2 is a detailed section of the roller surface on an enlarged scale;

FIG. 3 is a partial view of the roller in partially axial section and on a further enlarged scale;

FIG. 4 is an enlarged showing of a partial cross-sectional view of the roller or roll.

DETAILED DESCRIPTION OF THE INVENTION

Figure 5:
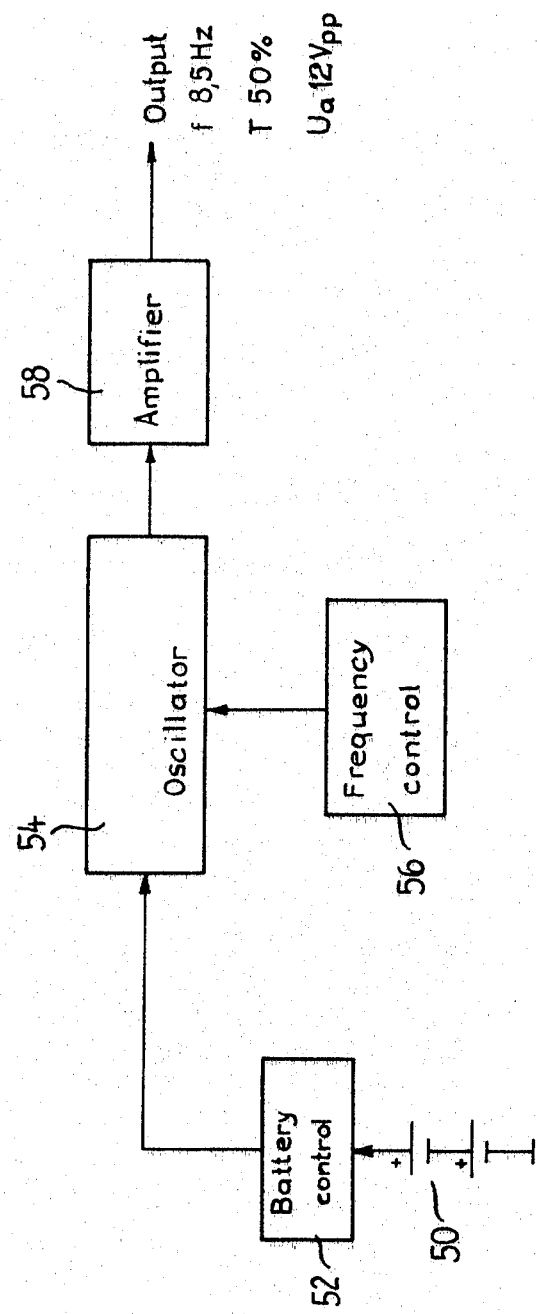
FIG. 5 is a block circuit diagram illustrating circuitry for generating the direct-current voltage pulses.

According to the showing of FIG. 1 the apparatus embodies a handle 1 in which the voltage pulse source 2, indicated in phantom lines, is accommodated. An exemplary embodiment of circuitry for generating the direct-current voltage pulses has been shown in FIG. 5. For instance such may comprise a power source, for example in the form of batteries 50 feeding the output via a battery control 52 to the input side of an oscillator 54 controlled by a frequency control 56. The output of the oscillator is delivered to an amplifier 58 and at the output of the amplifier there appear the modified direct-current voltage pulses having the characteristics noted heretofore. These are supplied via a current infeed means 3 to a roller-shaped electrode 4 (briefly referred to as a roller). The enlarged showing of the surface of the roller 4 portrayed in FIG. 2 reveals that the same is composed of substantially pyramid-shaped parts 5 (briefly referred to as pyramids). These pyramids are arranged in rows oriented along the surface lines. In contrast to the illustration of FIG. 2 the rows can be offset relative to one another as has been shown for the arrangement of FIGS. 3 and 4. In this case, viewed in the peripheral direction, the tips of the pyramids are always located in the center between two neighboring pyramids of the next row. Significant in this respect is that the spacing between the geometric tips of one pyramid to the tips of the neighboring pyramid in the adjacent rows amounts to 6.955mm.

The pyramids do not have a geometric tip but rather a flattened tip, in the form of a square of an edge or side length amounting to 0.5 mm.

The voltage pulses are supplied to the thus shaped tips 6. The voltage course is square wave, and the pulse duration is essentially equal to the time span between two pulses, or stated in another way, the pulse duration equals one-half of the pulse period duration. This means that the expression "square wave shaped course" is to be understood in the narrower sense of the word. However, the relationship between the pulse duration and the time spacing of two pulses can advantageously amount to 60 : 40.

With the exception of the flattened tips 6 of the pyramids the roller possesses an electrically non-conductive surface. The same holds true for the handle 1. Due to this measure and the previously described measures there can be realized a controlled electrotherapeutic treatment with very few contact points in an exact predetermined arrangement. Of course, it should be evident that there is necessary a second electrode which can be connected with the voltage source. A further connection can be provided for a single electrode, for instance in the form of a push-button or pressure pin. Also for such there are applicable the previously specified requirements concerning the amplitude and the frequency of the direct-current voltage pulses. To insure maintenance of these parameters it is recommended to equip the apparatus with a luminescent control which—if desired by means of pulsating light—indicates that the previously mentioned operating conditions are being maintained and also indicates by means of an appropriate circuit dropping of the amplitude to less than 6 volts.

While there are shown and described present preferred embodiments of the invention, it is to be distinctly understood that the invention is not limited thereto, but may be otherwise variously embodied and practiced within the scope of the following claims.

Accordingly, what is claimed is:

1. An electrotherapeutic apparatus for external applications comprising circuit means for generating direct-current voltage pulses hving an amplitude between 4 and 22 volts and a frequency of about 8.5 Hz, said circuit means including circuitry for producing a square wave voltage course of said pulses having a pulse duration substantially equal to the time span between two successive pulses, means for applying said pulses to a living body, said pulse applying means comprising an electrode in the form of a roller, said roller having a surface formed of substantially pyramid-shaped electrically conductive parts including tips, the pyramid-shaped parts at the region of said tips having substantially square flattened portions, said flattened portions having an edge length of approximately 0.5 mm, said pyramid-shaped parts being arranged in adjacent rows, the pyramid-shaped parts of said adjacent rows being offset with respect to each other, the spacing between the geometric tips of the pyramid-shaped parts neighboring one another and located in successive rows being 6.955 mm and means connected between said circuit means and said electrode for supplying said voltage pulses to the tips of said pyramid-shaped parts.

2. The apparatus as defined in claim 1, wherein the amplitude is in the order of between 6 and 16 volts.

3. The apparatus as defined in claim 2, wherein the amplitude amounts of 12 volts.

4. The apparatus as defined in claim 1, wherein said circuit means comprises an oscillator, frequency control means for controlling said oscillator, an amplifier having an ouput, said oscillator having an ouput said in circuit with said amplifier, the output of said amplifier supplying said direct-current voltage pulses.

* * * * *